(12) United States Patent
Korytkowski

(10) Patent No.: US 7,686,614 B2
(45) Date of Patent: Mar. 30, 2010

(54) DENTAL HANDPIECE DRIVE TRAIN WITH NON-INTERSECTING AXES

(75) Inventor: Zdzislaw W. Korytkowski, Island Lake, IL (US)

(73) Assignee: Dentsply International Inc., York, PA (US)

( * ) Notice: Subject to any disclaimer, the term of this patent is extended or adjusted under 35 U.S.C. 154(b) by 117 days.

(21) Appl. No.: 11/420,613

(22) Filed: May 26, 2006

(65) Prior Publication Data

US 2007/0275349 A1    Nov. 29, 2007

(51) Int. Cl.
*A61C 1/12* (2006.01)

(52) U.S. Cl. ........................................ 433/114; 433/133

(58) Field of Classification Search ................ 433/105, 433/103, 112, 114, 124, 131, 132, 133; 74/460, 74/462, 466
See application file for complete search history.

(56) References Cited

U.S. PATENT DOCUMENTS

| 2,923,060 | A | * | 2/1960 | Staunt ........................ 433/133 |
| 3,229,369 | A | * | 1/1966 | Hoffmeister et al. ........ 433/105 |
| 3,262,331 | A | * | 7/1966 | Breuer ...................... 74/412 R |
| 3,368,279 | A | * | 2/1968 | Weissman .................. 433/105 |
| 3,436,980 | A | * | 4/1969 | Loge et al. .................... 74/352 |
| 3,504,565 | A | * | 4/1970 | Lichtenauer et al. .......... 74/458 |
| 3,579,833 | A | * | 5/1971 | Colombo et al. ............ 433/121 |
| 3,631,742 | A |   | 1/1972 | Hoffmeister |
| 4,147,072 | A | * | 4/1979 | Mullins ........................ 74/416 |
| 4,251,212 | A | * | 2/1981 | Worschischek et al. ..... 433/126 |
| 4,266,933 | A | * | 5/1981 | Warden et al. ................. 433/82 |
| 4,321,041 | A | * | 3/1982 | Lustig et al. ................. 433/133 |
| 4,475,889 | A | * | 10/1984 | Garcia et al. ................. 433/103 |
| 4,693,685 | A | * | 9/1987 | Pernot ........................ 433/105 |
| 5,096,418 | A | * | 3/1992 | Coss .............................. 433/29 |
| 5,281,138 | A |   | 1/1994 | Rosenstatter |
| 5,429,558 | A |   | 7/1995 | Lagarde |
| 5,531,599 | A |   | 7/1996 | Bailey |
| 5,569,034 | A |   | 10/1996 | Meller et al. |
| 5,616,029 | A |   | 4/1997 | Suzuki |
| 6,030,216 | A |   | 2/2000 | Rosenstatter |
| 6,409,507 | B1 | * | 6/2002 | Postal et al. ................. 433/118 |
| 7,074,041 | B2 | * | 7/2006 | Kuhn ........................ 433/127 |
| 7,179,087 | B2 | * | 2/2007 | Kuhn ........................ 433/126 |
| 7,217,129 | B2 | * | 5/2007 | Lingenhole et al. ......... 433/132 |
| 7,416,410 | B2 | * | 8/2008 | Kuhn ........................ 433/105 |
| 2005/0089817 | A1 | * | 4/2005 | Kuhn ........................ 433/114 |

FOREIGN PATENT DOCUMENTS

DE    9307903 U1    9/1993
EP    0525649 A1 *  2/1993

* cited by examiner

*Primary Examiner*—Ralph A Lewis
(74) *Attorney, Agent, or Firm*—McNees Wallace & Nurick, LLC

(57) ABSTRACT

A dental handpiece includes a body having a first portion and a second portion, the first and second portions disposed at an ergonomic angle to each other. A drive gear extends from the second portion toward the first portion. The drive gear has a first axis of rotation and rotatably drives at least one driven gear having a second axis of rotation. The at least one driven gear is operatively connected to a bur disposed in the first portion to rotatably drive the bur about a third axis of rotation. The drive gear and the at least one driven gear do not include a taper gear or a face gear.

11 Claims, 5 Drawing Sheets

DENTAL HANDPIECE DRIVE TRAIN WITH NON-INTERSECTING AXES

FIELD OF THE INVENTION

The present invention is directed to a drive train of meshing gears for use in an apparatus, and more specifically to a drive train of meshing gears for use in dental handpieces.

BACKGROUND OF THE INVENTION

Dental professionals, for a number of different dental procedures, use powered dental handpieces containing a rotating head for receiving a dental tool. Preferably, the handpiece is constructed with an ergonomically friendly shape to reduce the user's stress level associated with gripping the handpiece for extended periods of time. Gears attached to rotatable shafts disposed inside the handpiece mesh with each other to rotatably drive the dental tool from a driving source associated with the handpiece.

As shown in FIG. 1, a typical ergonomic handpiece 10 includes a body 20 having a first portion 21 extending to a head 27 that is disposed at an angle of 21 degrees with a second portion 25. A drive train 15 disposed inside body 20 must therefore conform to the spatial constraints of the angled inner walls of the handpiece body, as shown in FIG. 1. A housing 23 rotatably carries a drive gear 22 about an axis 24 that is rotatably driven by a source (not shown). Drive gear 22 meshes with a gear 28 at one end of a shaft 26 that includes a gear 30 at the opposite end of shaft 26. Shaft 26 is configured to rotate about an axis 31. Gear 30 meshes with a gear 34 disposed at one end of shaft 32 that includes a gear 36 at the opposite end of shaft 32. Shaft 32 is configured to rotate about an axis 38. Gear 36 meshes with gear 42 at one end of shaft 40 that includes a collet 44 at the opposite end of a shaft 40 for securing a dental tool therein. Shaft 40 is configured to rotate about an axis 46. Thus, in response to the drive source, drive gear 22 and shafts 26, 32, 40 are urged into rotational movement about respective axes 24, 31, 38, 46 so that a dental tool mounted in collet 44 is rotatably carried about axis 46.

Axes 24, 31, 38, 46 of drive train 15 are disposed in coplanar alignment. Coplanar is defined herein to indicate that axes 24, 31, 38, 46 are each coincident with a single, vertically disposed plane. As shown in FIG. 1, at least one axis of axes 24, 31, 38, 46 is also nonparallel with the other coplanar axes, resulting in the drive train 15 having substantial cost and performance disadvantages. By virtue of the ergonomically friendly angle formed between body portions 21, 25, axes 24, 31, 38 that extend only through portions of body 20 are not parallel to each other. As shown in FIG. 1, axes 31, 38 are not parallel to each other. Because gears 30, 34 rotating about respective axes 31, 38 mesh, at least one, if not both, of gears 30, 34 are tapered. Tapered gears are more expensive to produce, since special methods of manufacture are required. Alternately, it may be possible to substitute face gears in place of tapered gears, but face gears also suffer from the same disadvantages as tapered gears. Additionally, the nonparallel arrangement of drive gear 22 and axes 24, 26, 38 are especially sensitive to mounting distances and angle errors and tend to produce a higher amount of noise during operation, especially when either tapered or face gears are used.

What is needed is a drive train for an ergonomic dental handpiece that does not require either a tapered or face gear for gears disposed adjacent to the junction between the first and second portions of the handpiece.

SUMMARY OF THE INVENTION

The present invention relates to a dental handpiece including a body having a first portion and a second portion, the first and second portions disposed at an ergonomic angle to each other. A drive gear extends from the second portion toward the first portion. The drive gear has a first axis of rotation and rotatably drives at least one driven gear having a second axis of rotation. The at least one driven gear is operatively connected to a bur disposed in the first portion to rotatably drive the bur about a third axis of rotation. The drive gear and the at least one driven gear do not include a taper gear or a face gear.

The present invention further relates to a dental handpiece including a body having a first portion and a second portion, the first and second portions disposed at an ergonomic angle to each other. A drive gear extends from the second portion toward the first portion, the drive gear having a first axis of rotation. The drive gear rotatably drives a first driven gear having a second axis of rotation, the first driven gear fixedly connected to a second gear also having the second axis of rotation. The second gear rotatably drives a third gear having a third axis of rotation, the third gear operatively connected to a bur disposed in the first portion, the bur having a fourth axis of rotation. The second axis of rotation does not intersect the first axis of rotation or the third axis of rotation.

The present invention still further relates to a dental handpiece including body having a first portion and a second portion, the first and second portions disposed at an ergonomic angle to each other. A cylindrical drive gear has a first axis of rotation, the drive gear rotatably driving at least one cylindrical driven gear having a second axis of rotation. The at least one driven gear is operatively connected to a bur disposed in the first portion to rotatably drive the bur about a third axis of rotation.

An advantage of the present invention is that none of the drive train gears disposed adjacent to the junction between the first and second portions are tapered, allowing the device to be manufactured inexpensively and without the drawbacks of tapered drive train gears.

A further advantage of the present invention is that none of the drive train gears disposed adjacent to the junction between the first and second portions are face gears, also allowing the device to be manufactured inexpensively and without the drawbacks of full face drive train gears.

A still further advantage of the present invention is that the drive train gears operate more quietly.

Other features and advantages of the present invention will be apparent from the following more detailed description of the preferred embodiment, taken in conjunction with the accompanying drawings which illustrate, by way of example, the principles of the invention.

BRIEF DESCRIPTION OF THE DRAWINGS

Wherever possible, the same reference numbers will be used throughout the drawings to refer to the same or like parts.

DETAILED DESCRIPTION OF THE INVENTION

Figure 1:
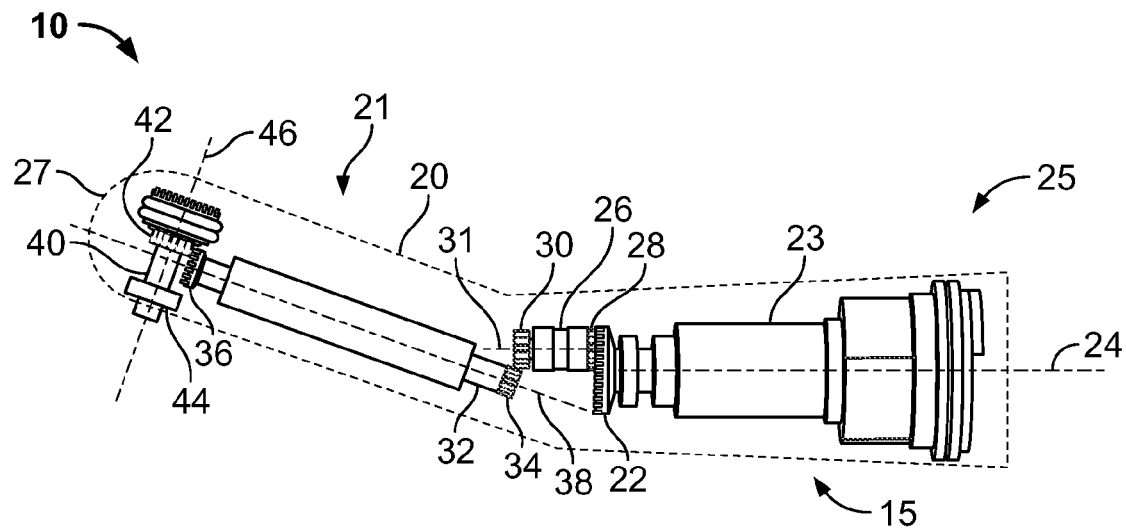
FIG. 1 is an elevation view of a prior art dental handpiece.
Figure 2:
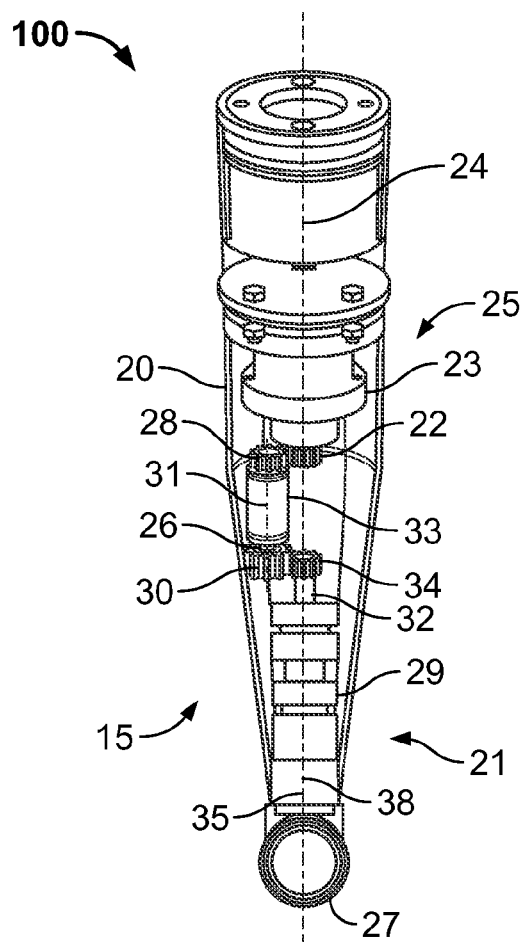
FIG. 2 is a partial cutaway top view of a dental handpiece of the present invention.
Figure 3:
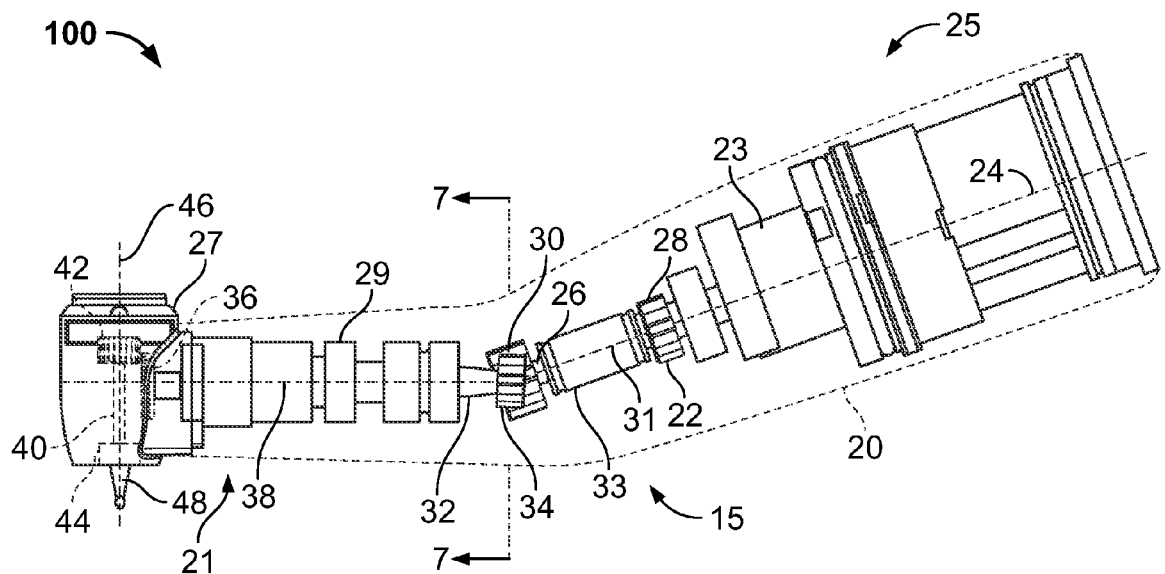
FIG. 3 is an elevation view of the dental handpiece of FIG. 2 of the present invention.
Figure 4:
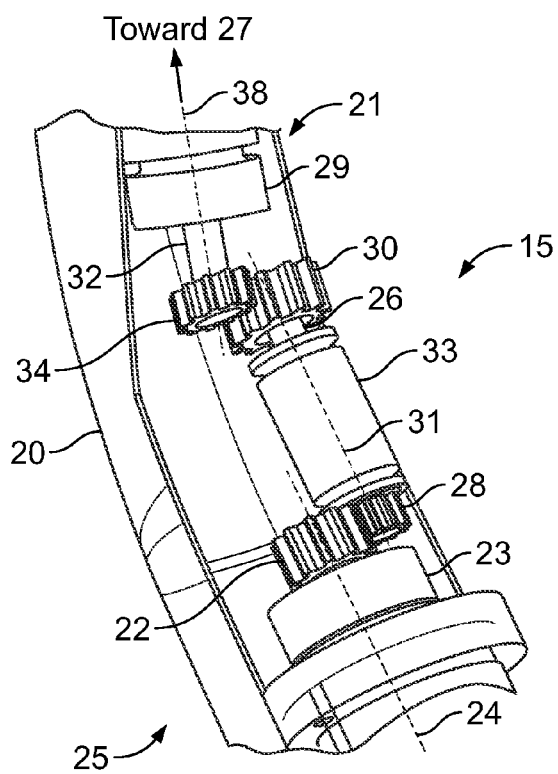
FIG. 4 is an enlarged partial cutaway perspective view of the dental handpiece of FIG. 2 of the present invention.

The present invention is directed to a dental handpiece 100 depicted in FIGS. 2-4. Handpiece 100 includes a body 20 having a first portion 21 extending to a head 27 that is disposed at an angle of about 21 degrees with a second portion 25. The angle between first and second portions 21, 25 is configured to ergonomically conform with a user's hand while grasping the handpiece 100. A drive train 15 disposed inside body 20 must therefore conform to the spatial constraints of the angled inner walls of the handpiece body 20, as shown in FIG. 2. A housing 23 rotatably carries a drive gear 22 allowing rotation about an axis 24 that is rotatably driven by a source, such as a pneumatic, hydraulic or electric motor (not shown). Drive gear 22 meshes with a gear 28 at one end of a shaft 26 that includes a gear 30 at the opposite end of shaft 26. A housing 33 rotatably carries shaft 26 allowing rotation about an axis 31. Gear 30 meshes with a gear 34 disposed at one end of shaft 32 that includes a gear 36 at the opposite end of shaft 32. Preferably, a housing 29 rotatably carries shaft 32 allowing rotation about an axis 38. Housings 23, 33, 29 preferably contain bearings to provide smooth rotational movement by respective drive gear 22 and shafts 26, 32. Gear 36 meshes with gear 42 at one end of a shaft 40 that includes a collet 44 at the opposite end of shaft 40 for securing a dental tool 48 therein as shown in FIG. 3. Shaft 40 is configured to rotate about axis 46, which is substantially perpendicular to axis 38. Thus, in response to the drive source, drive gear 22 and shafts 26, 32, 40 are urged into rotational movement about respective axes 24, 31, 38, 46 so that dental tool 48 mounted in collet 44 is rotatably carried about axis 46. Stated another way, drive gear 22 drives gear 28 (driven gear), gear 30 drives gear 34 (driven gear), and gear 36 drives gear 42 (driven gear). Although, strictly speaking, gears 30 and 36 are commonly referred to as drive gears, only gear 22 is consistently designated as a drive gear 22, both for simplicity, and due to the fact that drive gear 22 is coupled with the drive source.

Figure 7:
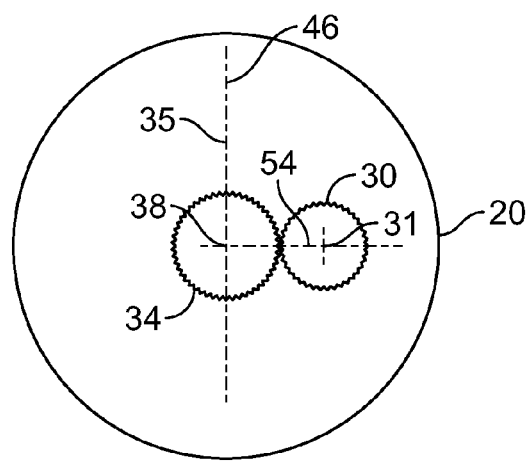
FIG. 7 is a cross section along line 7-7 of FIG. 3 of an embodiment of a dental handpiece of the present invention.

The arrangement of drive train 15 differs from previous drive train arrangements in at least one aspect; rotational axis 31 is not coplanar with axes 24, 38 nor with 46. Additionally, axis 31 can be skewed with respect to axis 24, i.e., non intersecting, non-coplanar lines. As shown for one embodiment in FIGS. 2-4, a plane 35 (see FIG. 2) is defined by axes 46, 38 (see FIG. 3). Additionally, axis 24 can be, but is not necessarily, coplanar to plane 35. However, axis 31 is not coplanar with the plane defined by axes 46, 38. As shown in FIG. 7, which is taken along line 7-7 of FIG. 3, gear 30 meshes with gear 34 at about a 3 o'clock position with respect to axis 38 and axis 46 (12 o'clock and 6 o'clock) as indicated by a line 54 extending perpendicular from axis 38 to axis 31. Alternately, gear 30 can be disposed to mesh with gear 34 at about a 9 o'clock position with respect to axis 46. Due to rotational axes 31, 38 not intersecting, the teeth of respective meshing gears 30, 34 are not required to be tapered, thus eliminating the disadvantages associated with tapered gears, including the additional expense of forming the taper on the gears, as well as increased noise associated with operation of tapered gears. As used herein, such non-tapered gears are referred to as cylindrical gears, having a constant cross section taken perpendicular to the axis of rotation. It is understood by those having ordinary skill in the art that in the case of a helical gear, cross sections taken at different locations of the gear will appear to be rotated about the axis of rotation of the gear. Further, when the cylindrical gear has radially extending teeth that are oriented parallel to the axis of rotation of the gear, the gear is referred to as a spur gear. For purposes herein, cylindrical gears do not include gears having a taper. Tapered gears include all bevel gears and can include face gears, i.e., face gears that are beveled. It is to be understood that although disposing gear 30 with meshing gear 34 has been shown at 90 degree angles from plane 35 defined by axes 46, 38, as measured from line 54 which is perpendicular to axis 38 and extends from axis 38 to axis 31, the angle between line 54 and plane 35 can be disposed at any number of other positions defining acute angles that also do not require either of meshing gears 30, 34 to be tapered.

It is to be understood that the gears which are cylindrical, i.e., non-tapered and not including beveled face gears, are those disposed adjacent to the junction between first portion 21 and second portion 25. Typically, for example, gear 36, which meshes with gear 42 in the head of the handpiece, is a face gear. However, since gear 36 is disposed adjacent to the head of the handpiece, gear 36 cannot be adjacent to the juncture of the first and second portions 21, 25. The gears adjacent to the first and second portions 21, 25 and the shafts interconnecting those gears will typically account for most, if not all of the angular transition between the first and second portions 21, 25. It is of critical importance that the meshing gears adjacent the junction between the first and second portions 21, 25 are cylindrical, for the advantageous reasons previously discussed.

Three examples of gear train constructions that are compatible with a handpiece as shown in FIGS. 2-4 are provided. It is understood by those having ordinary skill in the art that the helix angle of the associated gear is the angle between the gear teeth and the axis of rotation of the gear, unless a spur gear is used, in which case the angle between the gear teeth and the axis of rotation of the gear is zero degrees.

EXAMPLE 1

Drive gear 22: spur gear
Gear 28: spur gear
Gear 30: 10.5°
Gear 34: 10.5°

EXAMPLE 2

Drive gear 22: spur gear
Gear 28: 7°
Gear 30: 7°
Gear 34: 7°

EXAMPLE 3

Drive gear 22: 3.5°
Gear 28: 3.5°
Gear 30: 3.5°
Gear 34: 3.5°

It is also to be understood that any number of other combinations of gears 22, 28, 30, 34 can be employed that is compatible with the angular ergonomic arrangement of 21 degrees to balance cost, noise level, center distances between gears, strength and shape of the handpiece. However, in case a new handpiece angular arrangement is used that deviates from the 21 degree standard, it is to be understood that such deviations can simply be incorporated into helix angle arrangements that are compatible with the new handpiece arrangement.

Figure 5:
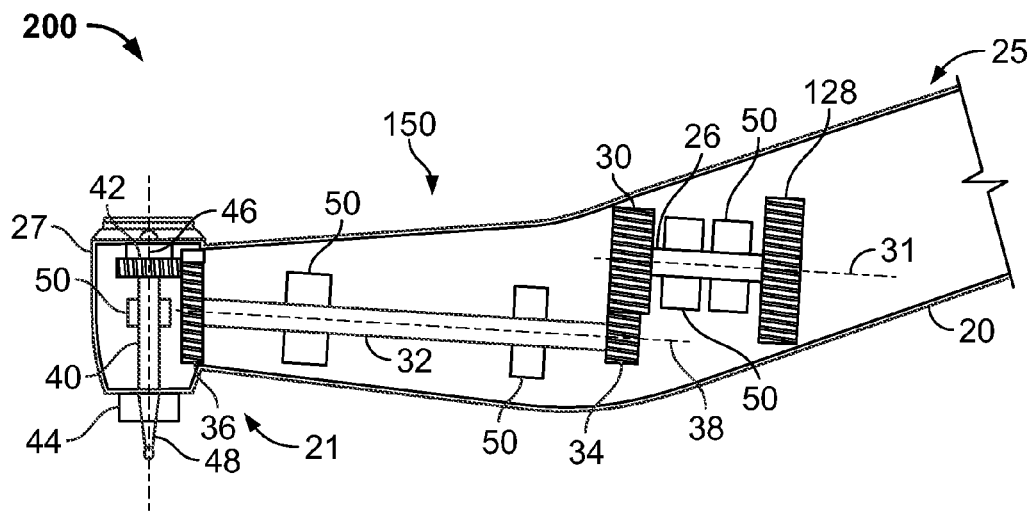
FIG. 5 is an elevation view of an embodiment of a dental handpiece of the present invention.

In an alternate embodiment, as shown in FIG. 5, a handpiece 200 has a drive train 150 that is configured differently from drive train 15, but maintaining the advantageous gearing arrangements, i.e., the meshing gears do not have a taper. Shaft 26 includes a turbine 128 at one end and a gear 30 at the opposite end that is rotatably carried by bearings 50 about axis 31. Turbine 128 is in communication with high speed gas from a source (not shown) that flows inside body 20 past the turbine 128, urging shaft 26 into rotational movement about axis 31. Gear 34, disposed in meshing engagement with gear 30, is positioned at one end of shaft 32, with gear 36 at the opposite end of shaft 32. Shaft 32 is rotatably carried about axis 38 by bearings 50. Similarly, gear 42 is disposed at one end of shaft 40 in meshing engagement with gear 36, with collet 44 disposed adjacent the opposite of shaft 40 and rotatably carried by bearings 50. In response to the high speed gas source flowing inside body 20, meshing gears 30, 34 and 36, 42 urge axes 31, 38, 46 into rotational movement. However, in the gearing arrangement as shown in FIG. 5, axes 31 and 38 can be parallel while still fitting within the envelope defined by body 20, with axis 46 being substantially perpendicular to axes 31, 38. By virtue of the axes 31, 38 remaining substantially parallel to each other, meshing gears 30, 34 not only do not require a taper, but both gears can also define spur gears, i.e., a gear with radial teeth parallel to its axis, which are less expensive to produce.

Figure 6:
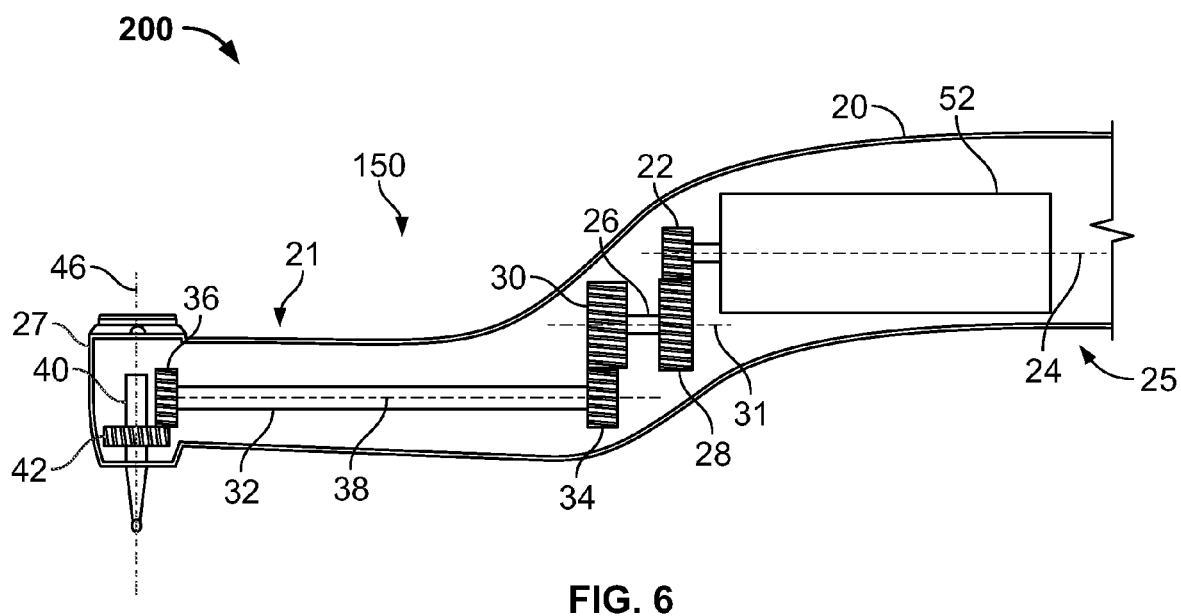
FIG. 6 is an elevation view of an embodiment of a dental handpiece of the present invention.

In a further embodiment, as shown in FIG. 6, axes 24, 31, 38 are preferably parallel to each other. The difference between the handpiece embodiments of FIGS. 5 and 6 is that the FIG. 6 embodiment is rotatably driven by a motor 52, such as an electric motor, versus high pressure gas, so that drive gear 22 urges gear 28 into rotational movement.

It is to be understood that while gears 28, 30 are shown as separate gears, 28, 30 can be combined into a single elongate gear.

Figure 8:
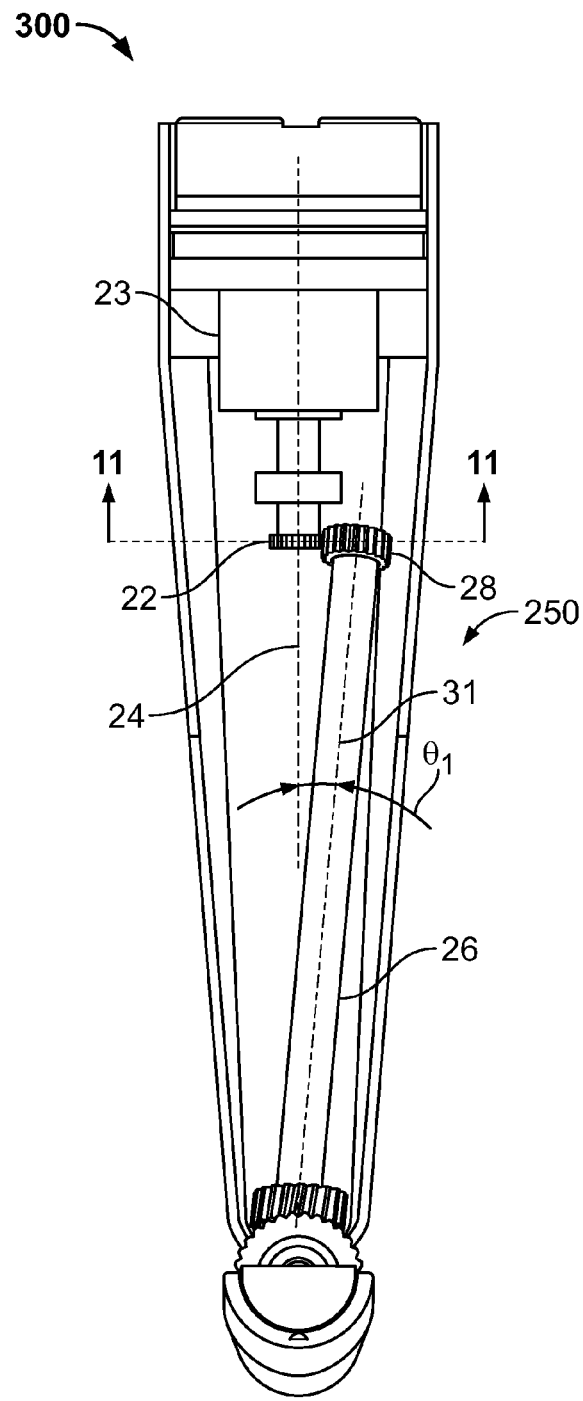
FIG. 8 is a partial cutaway perspective view of an embodiment of a dental handpiece of the present invention.
Figure 9:
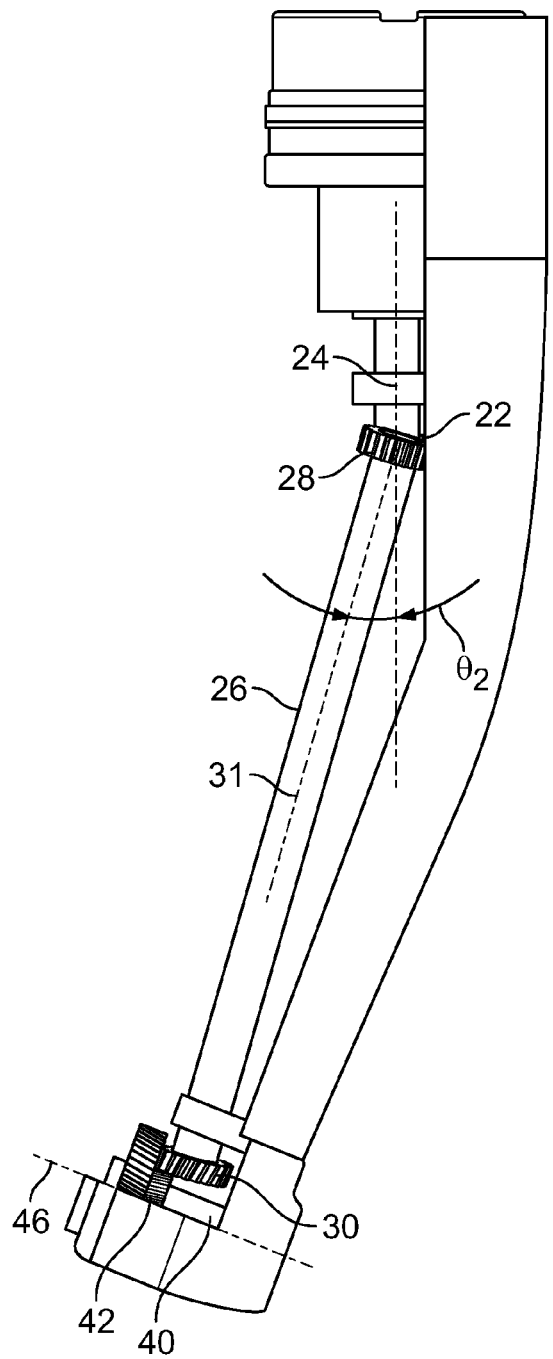
FIG. 9 is a partial cutaway side view of a dental handpiece of FIG. 8 of the present invention.
Figure 10:
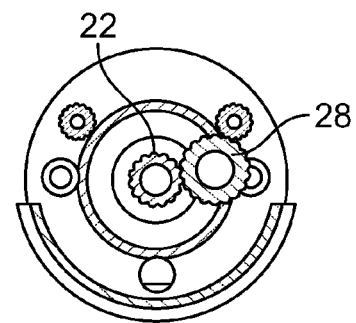
FIG. 10 is a cross section along line 11-11 of FIG. 8 of an embodiment of a dental handpiece of the present invention.

In an alternate embodiment, as shown in FIGS. 8-10, a handpiece 300 has a drive train 250 that is configured differently from drive train 15, but maintaining the advantageous gearing arrangements, i.e., the meshing gears do not have a taper. Similar to drive train 15 previously discussed, drive train 250 includes housing 23 that rotatably carries drive gear 22 allowing rotation about axis 24 which is rotatably driven by a source. Drive gear 22 meshes with gear 28 at one end of shaft 26 that includes gear 30 at the opposite end of shaft 26. However, in drive train 250, gear 30 meshes with gear 42 at one end of shaft 40 that is configured to rotate about axis 46, also as previously discussed. In other words, for drive train 250, shaft 32 having gears 32, 36 disposed at opposite ends thereof has been removed, as compared to drive train 15. By virtue of the elimination of shaft 32 and associated gears 32, 36, drive train 250 has fewer parts and a lower level of operating noise. As shown in FIGS. 8-9, shaft 26 defines a compound angle with axis 24, as axis 31 of shaft 26 is not parallel to axis 24, axis 31 forming transverse angles $\theta_1, \theta_2$ to axis 24. Stated another way, as shown in FIG. 9, $\theta_2$ represents the vertical component of the angle between axes 24, 31. Similarly, as shown in FIG. 8, $\theta_1$ represents the horizontal component of the angle between axes 24, 31. Since the magnitudes of angles $\theta_1, \theta_2$ are driven by the sizes of the gears and the desired profile of handpiece 300, it is to be understood that it may be possible for shaft 26 to be parallel to axis 24.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A dental handpiece comprising:
a body having a first portion and a second portion, the first and second portions disposed at an ergonomic angle to each other;
a drive gear extending from the second portion toward the first portion, the drive gear having a first axis of rotation, the drive gear rotatably driving a second gear having a second axis of rotation, the second gear fixedly connected to a third gear also having the second axis of rotation, the third gear rotatably driving a fourth gear, the fourth gear having a third axis of rotation, the fourth gear operatively connected to a bur disposed in the first portion, the bur having a fourth axis of rotation different from the third axis of rotation; and
wherein the second axis of rotation and the third axis of rotation are not coplanar, wherein the first axis of rotation and the third axis of rotation are not coaxial, and wherein the drive gear and the at least one driven gear do not include a taper gear or a face gear.

2. The dental handpiece of claim 1 wherein the drive gear is rotatably driven by a turbine.

3. The dental handpiece of claim 1 wherein the drive gear is rotatably driven by an electric motor.

4. The dental handpiece of claim 1 wherein the drive gear is rotatably driven by hydraulics.

5. The dental handpiece of claim 1 wherein the drive gear, second gear, third gear and the fourth gear operatively connected to the bur do not include a taper gear or a face gear.

6. The dental handpiece of claim 1 wherein the first axis of rotation and the second axis of rotation are coplanar.

7. The dental handpiece of claim 1 wherein the second gear comprises a first helix angle, the third gear comprises a second helix angle, wherein the fourth gear comprises a third helix angle, wherein the sum of the first helix angle, the second helix angle, and the third helix angle is approximately 21 degrees, and wherein the first helix angle, the second helix angle, and the third helix angle are approximately equal.

8. The dental handpiece of claim 7 wherein the drive gear is a spur gear.

9. The dental handpiece of claim 1 wherein the third gear comprises a first helix angle, wherein the fourth gear comprises a second helix angle, wherein the sum of the first helix angle and the second helix angle is approximately 21 degrees, and wherein the first helix angle and the second helix angle are approximately equal.

10. The dental handpiece of claim 9 wherein the second gear is a spur gear.

11. The dental handpiece of claim 1 wherein the second gear comprises a first helix angle, the third gear comprises a second helix angle, wherein the fourth gear comprises a third helix angle, wherein the drive gear comprises a fourth helix angle, wherein the sum of the first helix angle, the second helix angle, the third helix angle, and the fourth helix angle is approximately 14 degrees, and wherein the first helix angle, the second helix angle, the third helix angle, and the fourth helix angle are approximately equal.

* * * * *